(12) United States Patent
Sasaki et al.

(10) Patent No.: US 7,880,018 B2
(45) Date of Patent: Feb. 1, 2011

(54) EPOXY COMPOUND AND PRODUCTION PROCESS OF SAME

(75) Inventors: Nobutoshi Sasaki, Kawasaki (JP); Toshio Fujita, Kawasaki (JP); Hiroshi Uchida, Kawasaki (JP)

(73) Assignee: Showa Denko K.K., Tokyo (JP)

( * ) Notice: Subject to any disclaimer, the term of this patent is extended or adjusted under 35 U.S.C. 154(b) by 172 days.

(21) Appl. No.: 12/377,055

(22) PCT Filed: Aug. 13, 2007

(86) PCT No.: PCT/JP2007/066061

§ 371 (c)(1),
(2), (4) Date: Feb. 10, 2009

(87) PCT Pub. No.: WO2008/020637

PCT Pub. Date: Feb. 21, 2008

(65) Prior Publication Data

US 2010/0197936 A1    Aug. 5, 2010

(30) Foreign Application Priority Data

Aug. 15, 2006    (JP)    ............................. 2006-221648

(51) Int. Cl.
*C07D 303/06*    (2006.01)
*C07D 303/48*    (2006.01)
*C07D 491/12*    (2006.01)
*C07D 491/18*    (2006.01)

(52) U.S. Cl. .................. 548/406; 548/435; 548/509; 549/215; 549/506; 525/934

(58) Field of Classification Search .................. None
See application file for complete search history.

(56) References Cited

FOREIGN PATENT DOCUMENTS

JP    58-222160 A    12/1983

OTHER PUBLICATIONS

Tao, Z. et al., European Polymer Journal, 43:1470 (Apr. 2007).*
John L. Wood, et al, "Total Synthesis of (±)-Epoxysorbicillinol", Journal of the American Chemical Society, 2001, pp. 2097-2098, vol. 123, No. 9.

* cited by examiner

Primary Examiner—Yong Chu
Assistant Examiner—Michael Barker
(74) Attorney, Agent, or Firm—Sughrue Mion, PLLC

(57) ABSTRACT

A novel epoxy compound represented by the following general formula (I), and a production process thereof, is provided:

$$Y-(CH_2)_3-Si(OR^1)_n R^2{}_{3-n} \quad (I)$$

(wherein, Y is represented by any of the following formulas:

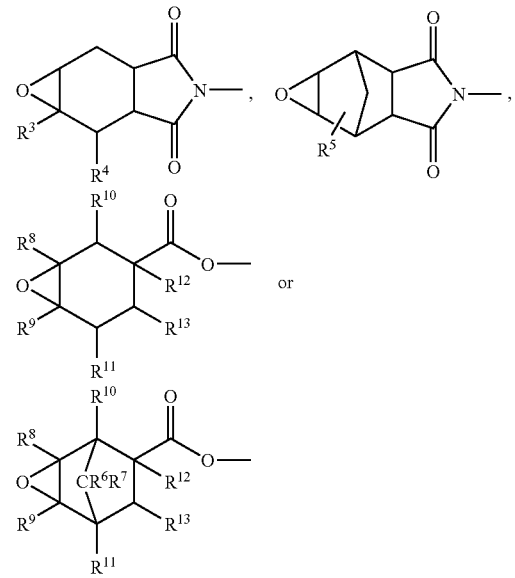

wherein, $R^1$ and $R^2$ represent alkyl groups having 1 to 5 carbon atoms, n represents an integer of 1 to 3, $R^3$ and $R^4$ represent hydrogen atoms, alkyl groups having 1 to 6 carbon atoms or trialkylsilyl groups having 1 to 4 carbon atoms, $R^5$ represents a hydrogen atom, an alkyl group having 1 to 6 carbon atoms or a trialkylsilyl group having 1 to 4 carbon atoms, $R^6$ to $R^{12}$ represent hydrogen atoms, alkyl groups having 1 to 6 carbon atoms or trialkylsilyl groups having 1 to 4 carbon atoms, and $R^{13}$ represents a hydrogen atom, an alkyl group having 1 to 6 carbon atoms, a trialkylsilyl group having 1 to 4 carbon atoms or an aryl group).

8 Claims, 12 Drawing Sheets

EPOXY COMPOUND AND PRODUCTION PROCESS OF SAME

TECHNICAL FIELD

The present invention relates to a novel epoxy compound that is useful as raw materials, such as sealing materials, formed materials, injection molding materials, laminated materials, composite materials, adhesives and powder coatings of electrical, electronic or optical components as well as in silane coupling agents, modified silicone and the like.

BACKGROUND ART

Epoxy compounds are used in a wide range of fields, including sealing materials, formed materials, injection molding materials, laminated materials, composite materials, adhesives and powder coatings of electrical, electronic and optical components since they allow the obtaining of cured articles having superior mechanical strength, moisture resistance and electrical properties. However, technical advances are placing even greater demands on the performance of epoxy compounds with respect to heat resistance and the like. Although N-(2,3-epoxypropyl)-perfluoro-4,5-epoxyphthalimide having an imide structure (see Non-Patent Document 1) has been previously proposed for the purpose of improving heat resistance, since epichlorhydrin is used in a step for producing an intermediate in the production process thereof, the presence of residual halogen in the finished product cannot be avoided, thereby making it undesirable as a production process for products of electronic material applications for which it is desired to reduce residual levels of halogens as much as possible. In addition, organopolysiloxanes or cyclic siloxanes have been proposed having a 3-glycidoxypropyl group or 2-(3,4-epoxycyclohexyl)ethyl group at the end of the molecular chain or in a side chain thereof for use as organopolysiloxanes having an epoxy group-containing organic group (see Patent Document 1).

[Non-Patent Document 1] R. Antoni, et al., Makromol. Chem., 194, 411 (1993)

[Patent Document 1] Japanese Unexamined Patent Publication No. H3-255130

DISCLOSURE OF THE INVENTION

Problems to be Solved by the Invention

However, there is still a need to provide a novel epoxy compound that is useful as raw materials, such as sealing materials, formed materials, injection molding materials, laminated materials, composite materials, adhesives and powder coatings of electrical, electronic or optical components.

Means for Solving the Problems

As a result of conducting extensive studies to solve the aforementioned problems, the inventors of the present invention were able to provide a novel epoxy compound represented by the following general formula (I):

(wherein, Y is represented by any of the following formulas:

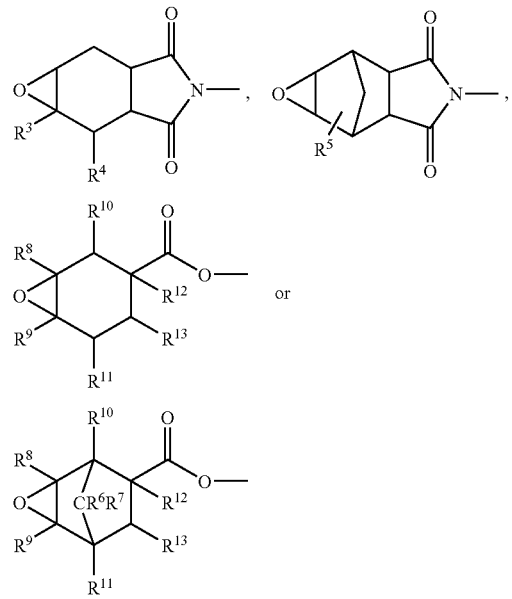

wherein, $R^1$ and $R^2$ represent alkyl groups having 1 to 5 carbon atoms, n represents an integer of 1 to 3, $R^3$ and $R^4$ represent hydrogen atoms, alkyl groups having 1 to 6 carbon atoms or trialkylsilyl groups having 1 to 4 carbon atoms, $R^5$ represents a hydrogen atom, an alkyl group having 1 to 6 carbon atoms or a trialkylsilyl group having 1 to 4 carbon atoms, $R^6$ to $R^{12}$ represent hydrogen atoms, alkyl groups having 1 to 6 carbon atoms or trialkylsilyl groups having 1 to 4 carbon atoms, and $R^{13}$ represents a hydrogen atom, an alkyl group having 1 to 6 carbon atoms, a trialkylsilyl group having 1 to 4 carbon atoms or an aryl group).

More specifically, the invention of the present application is as described in [1] to [8] below:

[1] an epoxy compound represented by the following general formula (I):

(wherein, Y is represented by any of the following formulas:

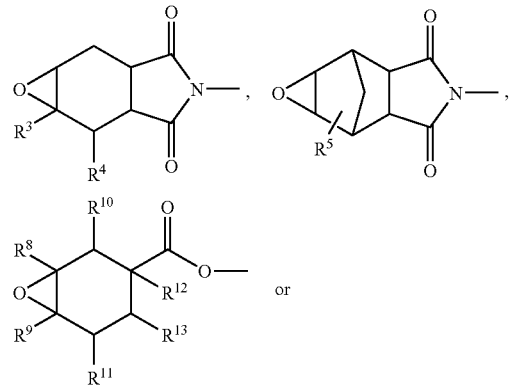

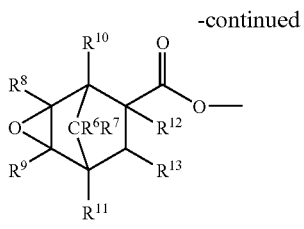

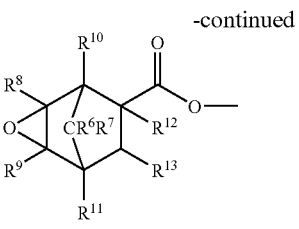

wherein, $R^1$ and $R^2$ represent alkyl groups having 1 to 5 carbon atoms, n represents an integer of 1 to 3, $R^3$ and $R^4$ represent hydrogen atoms, alkyl groups having 1 to 6 carbon atoms or trialkylsilyl groups having 1 to 4 carbon atoms, $R^5$ represents a hydrogen atom, an alkyl group having 1 to 6 carbon atoms or a trialkylsilyl group having 1 to 4 carbon atoms, $R^6$ to $R^{12}$ represent hydrogen atoms, alkyl groups having 1 to 6 carbon atoms or trialkylsilyl groups having 1 to 4 carbon atoms, and $R^{13}$ represents a hydrogen atom, an alkyl group having 1 to 6 carbon atoms, a trialkylsilyl group having 1 to 4 carbon atoms or an aryl group);

[2] the epoxy compound described in [1] above, wherein $R^1$ and $R^2$ are alkyl groups having 1 or 2 carbon atoms in the compound of general formula (I);

[3] the epoxy compound described in [1] above, wherein $R^3$ to $R^{12}$ are hydrogen atoms or methyl groups and $R^{13}$ is a hydrogen atom, methyl group or phenyl group in the compound of general formula (I);

[4] the epoxy compound described in [1] above, wherein $R^1$ and $R^2$ are alkyl groups having 1 or 2 carbon atoms, $R^3$ to $R^{12}$ are hydrogen atoms or methyl groups, and $R^{13}$ is a hydrogen atom, methyl group or phenyl group in the compound of general formula (I);

[5] A production process of the epoxy compound described in [1] above, comprising: reacting a silicon compound represented by the following general formula (II):

$$H{-}Si(OR^1)_n R^2_{3-n} \qquad (II)$$

(wherein, $R^1$ and $R^2$ respectively represent an alkyl group having 1 to 5 carbon atoms, and n represents an integer of 1 to 3), with an epoxy compound having a double bond represented by the following general formula (III):

$$Y{-}CH_2{-}CH{=}CH_2 \qquad (III)$$

(wherein, Y is represented by any of the following formulas:

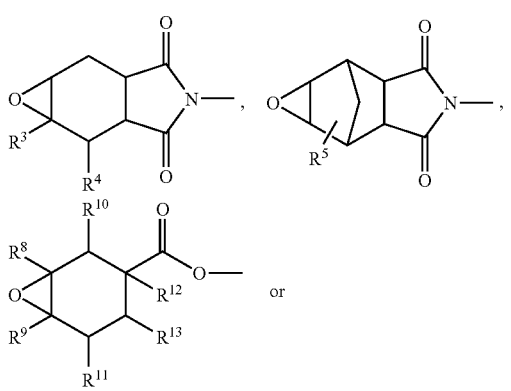

(wherein, $R^3$ and $R^4$ represent hydrogen atoms, alkyl groups having 1 to 6 carbon atoms or trialkylsilyl groups having 1 to 4 carbon atoms, $R^5$ represents a hydrogen atom, an alkyl group having 1 to 6 carbon atoms or a trialkylsilyl group having 1 to 4 carbon atoms, $R^6$ to $R^{12}$ represent hydrogen atoms, alkyl groups having 1 to 6 carbon atoms or trialkylsilyl groups having 1 to 4 carbon atoms, and $R^{13}$ represents a hydrogen atom, an alkyl group having 1 to 6 carbon atoms, a trialkylsilyl group having 1 to 4 carbon atoms or an aryl group) at 40 to 150° C.;

[6] the production process described in [5] above, wherein $R^1$ and $R^2$ are alkyl groups having 1 or 2 carbon atoms in the silicon compound of general formula (II);

[7] the production process described in [5] above, wherein $R^3$ to $R^{12}$ are hydrogen atoms or methyl groups and $R^{13}$ is a hydrogen atom, methyl group or phenyl group in the epoxy compound having a double bond of formula (III); and,

[8] the production process described in [5] above, wherein $R^1$ and $R^2$ are alkyl groups having 1 or 2 carbon atoms in the silicon compound of general formula (II), and $R^3$ to $R^{12}$ are hydrogen atoms or methyl groups and $R^{13}$ is a hydrogen atom, methyl group or phenyl group in the epoxy compound having a double bond of general formula (III).

BEST MODE FOR CARRYING OUT THE INVENTION

Figure 1:
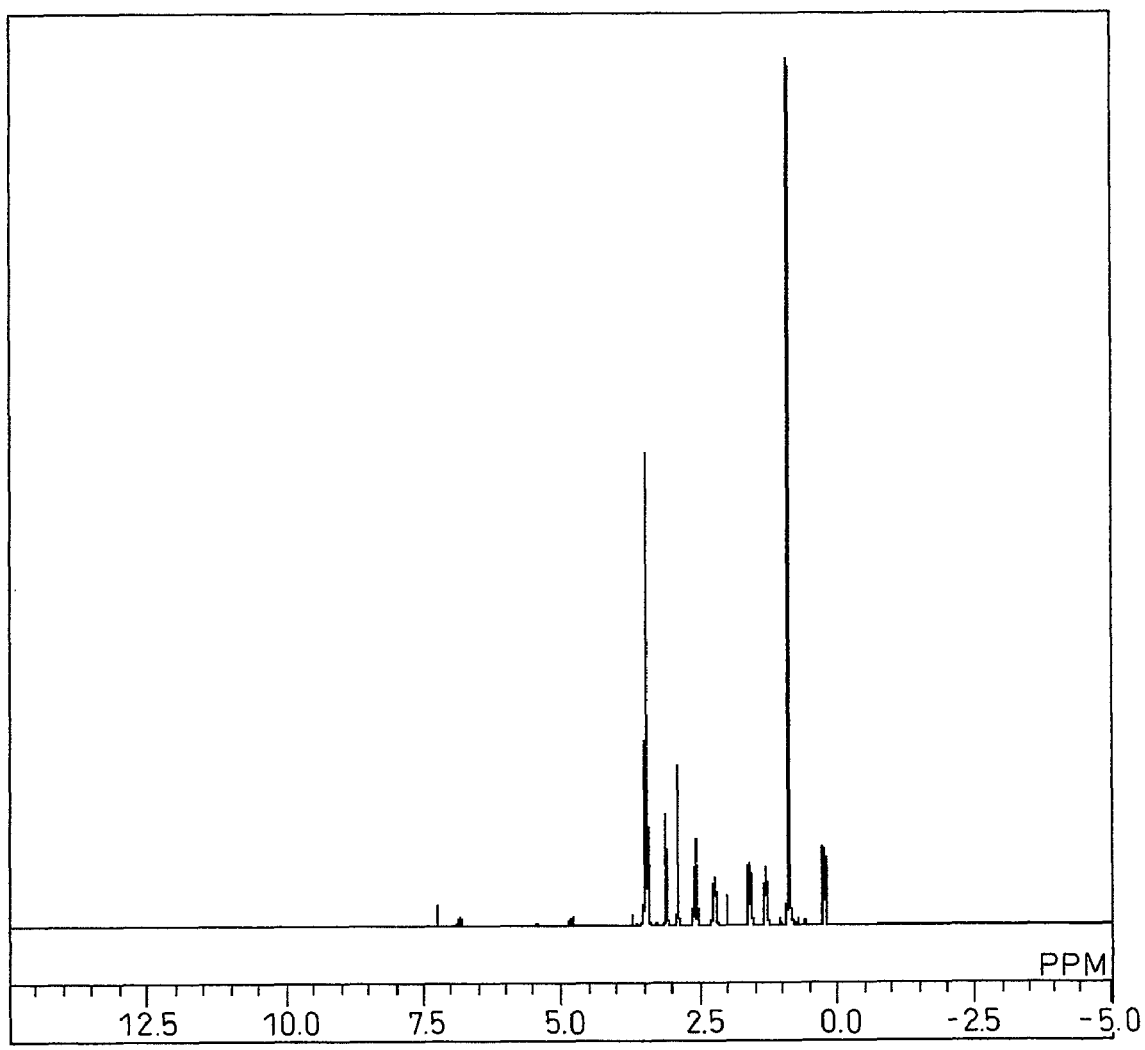
FIG. 1 is a chart showing the $^1$H-NMR spectrum of an epoxy compound represented by general formula (IV) obtained in Example 1.

The following provides a detailed explanation of the present invention. A novel epoxy compound obtained in the present invention is represented by the following general formula (I):

        (I)

(wherein, Y is represented by any of the following formulas:

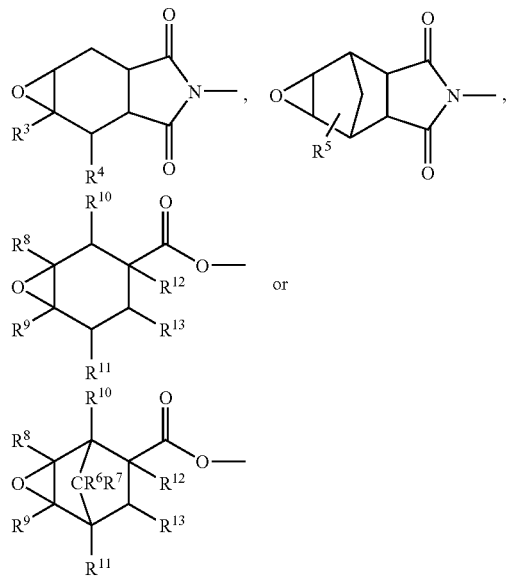

wherein, $R^1$ and $R^2$ represent alkyl groups having 1 to 5 carbon atoms, n represents an integer of 1 to 3, $R^3$ and $R^4$ represent hydrogen atoms, alkyl groups having 1 to 6 carbon atoms or trialkylsilyl groups having 1 to 4 carbon atoms, $R^5$ represents a hydrogen atom, an alkyl group having 1 to 6 carbon atoms or a trialkylsilyl group having 1 to 4 carbon atoms, $R^6$ to $R^{12}$ represent hydrogen atoms, alkyl groups having 1 to 6 carbon atoms or trialkylsilyl groups having 1 to 4 carbon atoms, and $R^{13}$ represents a hydrogen atom, an alkyl group having 1 to 6 carbon atoms, a trialkylsilyl group having 1 to 4 carbon atoms or an aryl group).

Specific examples of $R^1$ and $R^2$ in formula (I) include, but are not limited to, alkyl groups having 1 to 5 carbon atoms such as a methyl group, ethyl group, propyl group, isopropyl group, butyl group or pentyl group. $R^1$ and $R^2$ are more preferably methyl groups or ethyl groups.

Specific examples of $R^3$ and $R^4$ in formula (I) include, but are not limited to, hydrogen atoms, methyl groups, ethyl groups, propyl groups, isopropyl groups, butyl groups, isobutyl groups, tertiary butyl groups, pentyl groups, hexyl groups, trimethylsilyl groups, triethylsilyl groups and tertiary-butyldimethylsilyl groups. $R^3$ and $R^4$ are more preferably hydrogen atoms, methyl groups, trimethylsilyl groups or tertiary-butyldimethylsilyl groups, and even more preferably hydrogen atoms or methyl groups.

Specific examples of $R^5$ in formula (I) include, but are not limited to, a hydrogen atom, methyl group, ethyl group, propyl group, isopropyl group, butyl group, isobutyl group, tertiary-butyl group, pentyl group, hexyl group, trimethylsilyl group, triethylsilyl group and tertiary-butyldimethylsilyl group. $R^5$ is more preferably a hydrogen atom, methyl group, trimethylsilyl group or tertiary-butyldimethylsilyl group, and even more preferably a hydrogen atom or methyl group.

Specific examples of $R^6$ to $R^{12}$ in formula (I) include, but are not limited to, hydrogen atoms, methyl groups, ethyl groups, propyl groups, isopropyl groups, butyl groups, isobutyl groups, tertiary-butyl groups, pentyl groups, hexyl groups, trimethylsilyl groups, triethylsilyl groups and tertiary-butyldimethylsilyl groups. $R^6$ to $R^{12}$ are more preferably hydrogen atoms, methyl groups, trimethylsilyl groups or tertiary-butyldimethylsilyl groups, and even more preferably hydrogen atoms or methyl groups.

Specific examples of $R^{13}$ in formula (I) include a hydrogen atom, methyl group, ethyl group, propyl group, isopropyl group, butyl group, isobutyl group, tertiary-butyl group, pentyl group, hexyl group, trimethylsilyl group, triethylsilyl group, tertiary-butyldimethylsilyl group and phenyl group. $R^{13}$ is more preferably a hydrogen atom, methyl group, trimethylsilyl group, tertiary-butyldimethylsilyl group or phenyl group, and even more preferably a hydrogen atom, methyl group or phenyl group.

A novel epoxy compound of the present invention represented by general formula (I) can be produced by hydrosilylating a silicon compound represented by general formula (II) with an epoxy compound having a double bond represented by general formula (III) at 40 to 150° C.:

        (II)

(wherein, $R^1$ and $R^2$ respectively represent an alkyl group having 1 to 5 carbon atoms, and n represents an integer of 1 to 3); and

        (III)

(wherein, Y is represented by any of the following formulas:

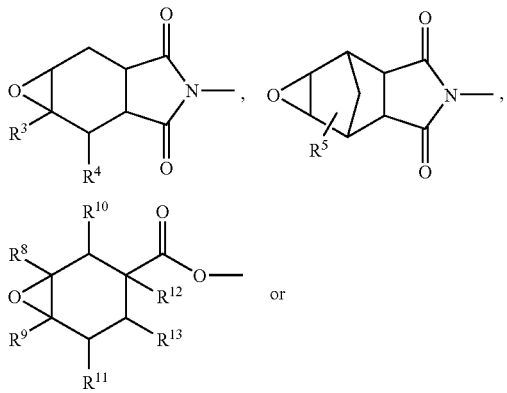

-continued

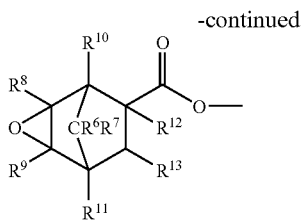

wherein, $R^3$ and $R^4$ represent hydrogen atoms, alkyl groups having 1 to 6 carbon atoms or trialkylsilyl groups having 1 to 4 carbon atoms, $R^5$ represents a hydrogen atom, an alkyl group having 1 to 6 carbon atoms or a trialkylsilyl group having 1 to 4 carbon atoms, $R^6$ to $R^{12}$ represent hydrogen atoms, alkyl groups having 1 to 6 carbon atoms or trialkylsilyl groups having 1 to 4 carbon atoms, and $R^{13}$ represents a hydrogen atom, an alkyl group having 1 to 6 carbon atoms, a trialkylsilyl group having 1 to 4 carbon atoms or an aryl group).

Specific examples of $R^1$ and $R^2$ in formula (II) include, but are not limited to, alkyl groups having 1 to 5 carbon atoms such as a methyl group, ethyl group, propyl group, isopropyl group, butyl group or pentyl group. $R^1$ and $R^2$ are more preferably methyl groups or ethyl groups.

Specific examples of $R^3$ and $R^4$ in formula (III) include, but are not limited to, hydrogen atoms, methyl groups, ethyl groups, propyl groups, isopropyl groups, butyl groups, isobutyl groups, tertiary butyl groups, pentyl groups, hexyl groups, trimethylsilyl groups, triethylsilyl groups and tertiary-butyldimethylsilyl groups. $R^3$ and $R^4$ are more preferably hydrogen atoms, methyl groups, trimethylsilyl groups or tertiary-butyldimethylsilyl groups, and even more preferably hydrogen atoms or methyl groups.

Specific examples of $R^5$ in formula (III) include, but are not limited to, a hydrogen atom, methyl group, ethyl group, propyl group, isopropyl group, butyl group, isobutyl group, tertiary-butyl group, pentyl group, hexyl group, trimethylsilyl group, triethylsilyl group and tertiary-butyldimethylsilyl group. $R^5$ is more preferably a hydrogen atom, methyl group, trimethylsilyl group or tertiary-butyldimethylsilyl group, and even more preferably a hydrogen atom or methyl group.

Specific examples of $R^6$ to $R^{12}$ in formula (III) include, but are not limited to, hydrogen atoms, methyl groups, ethyl groups, propyl groups, isopropyl groups, butyl groups, isobutyl groups, tertiary-butyl groups, pentyl groups, hexyl groups, trimethylsilyl groups, triethylsilyl groups and tertiary-butyldimethylsilyl groups. $R^6$ to $R^{12}$ are more preferably hydrogen atoms, methyl groups, trimethylsilyl groups or tertiary-butyldimethylsilyl groups, and even more preferably hydrogen atoms or methyl groups.

Specific examples of $R^{13}$ in formula (III) include a hydrogen atom, methyl group, ethyl group, propyl group, isopropyl group, butyl group, isobutyl group, tertiary-butyl group, pentyl group, hexyl group, trimethylsilyl group, triethylsilyl group, tertiary-butyldimethylsilyl group and phenyl group. $R^{13}$ is more preferably a hydrogen atom, methyl group, trimethylsilyl group, tertiary-butyldimethylsilyl group or phenyl group, and even more preferably a hydrogen atom, methyl group or phenyl group.

The blending ratio of the silicon compound represented by general formula (II) and the epoxy compound having a double bond represented by general formula (III) is arbitrary, and although there are no particular limitations thereon, in general, preferably 0.7 to 1.5 moles, and particularly preferably 0.9 to 1.1 moles, of the silicon compound represented by general formula (II) are blended to 1 mole of the epoxy compound having a double bond represented by general formula (II). If outside of this range, there are cases in which the reaction is economically disadvantageous since one of the raw materials is not used and remains unreacted.

A catalyst comprised of a transition metal or compound thereof in the manner of platinum, rhodium, palladium, nickel, iridium or ruthenium is selected as a catalyst used in the hydrosilylation reaction of the present invention. Specific examples of catalysts include chloroplatinic acid, various complexes of platinum, complexes of platinum and vinylsiloxane expelled of chlorine, Karsted's catalyst, various solutions of platinum compounds (those in which platinum is dissolved or dispersed in alcohol, ketone, ether, ester or aromatic hydrocarbon and the like), Speier's catalyst, catalysts loaded on various solids (such as silica gel or activated charcoal), Rh catalysts such as Wilkinson's catalyst and various types of complex catalysts of palladium, and there are no particular limitations on the type or form thereof. Although there are no particular limitations on the amount of platinum catalyst, it is such that there are preferably $1\times10^{-2}$ to $1\times10^{-8}$ times moles, and particularly preferably $1\times10^{-3}$ to $1\times10^{-6}$ times moles, of platinum atoms to 1 mole of hydroalkoxysilane. If the amount of platinum atoms is less than $1\times10^{-8}$ times moles, the reaction rate becomes quite slow, while if the amount of platinum atoms exceeds $1\times10^{-2}$ times moles, although the reaction rate increases, there are cases in which this is economically disadvantageous and results in the risk of the occurrence of ring-opening polymerization of the epoxy groups.

In the present invention, although a solvent may essentially not be used, there are no particular problems with the use of a solvent as a reaction solvent or as a solvent for a catalyst solution as necessary. If a solvent is used according to a need, such as for the purpose of dissolving or diluting a raw material, controlling the temperature of the reaction system, securing a required volume for stirring or facilitating addition of a catalyst, a solvent may be used in an arbitrary amount by arbitrarily selecting from saturated hydrocarbons such as pentane, hexane, isooctane, decane or cyclohexane, aromatic hydrocarbons such as toluene, xylene, mesitylene, ethylbenzene, decalin or tetralin, ethers such as diethylether or tetrahydrofuran (THF), esters and various types of silicones such as polydimethylsiloxanes. Furthermore, the solvent is not particularly limited to one type thereof, but rather two or more types may be used as a mixture.

The procedure for carrying out the hydrosilylation reaction of the present invention typically consists of charging an epoxy compound having a double bond represented by general formula (III) and an addition reaction catalyst into a reactor in which the interior thereof has been adequately replaced with a dry inert gas such as nitrogen gas. At this time, a solvent may also be charged into the reactor as necessary. Next, after heating to a prescribed temperature while stirring, a silicon compound represented by general formula (II) is added by dropping into the aforementioned mixture and allowed to react, and aging is carried out following completion of dropping until the reaction is completed. Furthermore, the process may also consist of charging the silicon compound represented by general formula (II) instead of the epoxy compound having a double bond represented by general formula (III) followed by adding the epoxy compound having a double bond represented by general formula (III) instead of the silicon compound represented by general formula (II). In addition, the process may also consist of adding a mixture of the silicon compound represented by general formula (II) and the epoxy compound having a double bond represented by general formula (III) to an addition reaction catalyst and suitable solvent, or the process may consist of charging all raw materials all at once followed by heating. In addition, the production process of the present invention can be applied to either a batch type, continuous type or semi-continuous type of reaction process.

The reaction temperature is preferably within the range of 20 to 200° C. and particularly preferably within the range of 40 to 150° C. If the reaction temperature is lower than 20° C., the reaction rate becomes slow which may prevent the reaction from being completed within a practical process time. In addition, if the reaction temperature exceeds 200° C., although the reaction rate increases, there is the possibility of the occurrence of ring-opening polymerization of epoxy groups of the epoxy compound having a double bond represented by general formula (III) and those of the target novel epoxy compound represented by general formula (I).

The pressure conditions are such that atmospheric pressure is typically adequate for carrying out the reaction, and is also preferably in terms of ease of operation and economy. However, the reaction may also be carried out under pressure as necessary.

The atmosphere within the reactor is preferably an inert gas such as nitrogen gas. Contamination by moisture (or air containing moisture) not only as a detrimental effect on the reaction, but also results in the risk of decreasing yield by causing hydrolysis of the silicon compound represented by general formula (II). Furthermore, there are also no particular problems with employing a known technology consisting of introducing an inert gas containing dry air or oxygen into the reactor atmosphere for the purpose of enhancing catalytic activity of the addition reaction catalyst.

The reaction time can be arbitrarily varied within the range of 0.1 to 100 hours according to the reaction temperature, pressure conditions, catalyst concentration or concentrations of raw materials in the reaction system.

Any commonly used method can be used to purify the product, examples of which include adsorptive separation, and more specifically, impurity or colored substance adsorption methods using an absorbent such as activated charcoal, acid clay or active clay, or column chromatography or thin layer chromatography, and more specifically, that using silica gel, aqueous silica gel, alumina, activated charcoal, titania or zirconia, and even more specifically, column chromatography using a packing material such as silica gel, aqueous silica gel or alumina. In addition, the reaction product can also be purified by distillation, and more specifically, vacuum distillation or molecular distillation. During distillation, there are no particular problems with carrying out known means for inhibiting ring-opening polymerization of epoxy groups of the novel epoxy compound represented by general formula (I) and a reaction raw material in the form of the epoxy compound having a double bond represented by general formula (III) during distillation by adding a small amount of an amine or sulfur-containing compound and the like to the reaction liquid prior to distillation. In addition, the reaction mixture may also be used as is since purification of the reaction product is not necessarily required depending on the purpose of use of the novel epoxy compound represented by general formula (I).

Although there are no particular limitations on the reaction vessel used in the present invention, it is preferably equipped with apparatuses such as a stirring apparatus, thermometer, reflux condenser and dropping apparatus.

EXAMPLES

Although the following provides a detailed explanation of the present invention using examples thereof, the present invention is not limited by these examples.

Reference Example 1

304.3 g of cis-4-cyclohexene-1,2-dicarboxylic acid anhydride and 280 g of toluene were charged into a 1 L four-mouth flask provided with a reflux condenser, thermometer, stirring apparatus, dropping funnel and oil bath. The entire amount of 116.5 g of allylamine were dropped therein over the course of 90 minutes from the dropping funnel in a nitrogen atmosphere, and after aging for 30 minutes, a Dean-Stark moisture separator was attached to a separable flask followed by heating and refluxing for 5 hours while removing trapped water using the oil bath maintained at 140° C. and then cooling to room temperature.

Solvent was removed from the contents of the flask using a rotary evaporator to obtain 344.3 g of a N-allyl-4-cyclohexene-1,2-dicarboxy crude product. This was then purified by vacuum distillation to obtain 273.5 g of pure N-allyl-4-cyclohexene-1,2-dicarboximide in the form of a colorless, clear liquid.

100.0 g of N-allyl-4-cyclohexene-1,2-dicarboximide, 2.44 g of methyltrioctylammonium hydrogen sulfate, 3.45 g of sodium tungstenate dihydrate and 0.58 g of aminomethylphosphonic acid were charged into a 500 mL three-mouth flask provided with a reflux condenser, thermometer, stirring apparatus, dropping funnel and oil bath. After heating using the oil bath maintained at a temperature of 90° C., 80 ml of 30% aqueous hydrogen peroxide were dropped in over the course of 180 minutes through the dropping funnel followed by aging for 4 hours. After cooling with an ice bath and removing the excess hydrogen peroxide with 300 ml of saturated aqueous sodium thiosulfate solution, the reaction mixture was extracted twice with 200 ml of ethyl acetate. The resulting ethyl acetate solution was dried overnight with anhydrous sodium sulfate followed by removing the solvent ethyl acetate using a rotary evaporator and purifying by column chromatography using a column packed with 25% aqueous silica gel to obtain 78.9 g of 4,5-epoxy-N-allylcyclohexane-1,2-dicarboximide.

Reference Example 2

100.0 g of 3-cyclohexene-1-carboxylic acid allyl, 2.34 g of methyltrioctylammonium hydrogen sulfate, 3.96 g of sodium tungstenate dihydrate and 0.45 g of aminomethylphosphonic acid were charged into a 500 mL three-mouth flask provided with a reflux condenser, thermometer, stirring apparatus, dropping funnel and oil bath. After heating using the oil bath maintained at a temperature of 90° C., 80 ml of 30% aqueous hydrogen peroxide were dropped in over the course of 180 minutes through the dropping funnel followed by aging for 4 hours. After cooling with an ice bath and removing the excess hydrogen peroxide with 300 ml of saturated aqueous sodium thiosulfate solution, the reaction mixture was extracted twice with 200 ml of ethyl acetate. The resulting ethyl acetate solution was dried overnight with anhydrous sodium sulfate followed by removing the solvent ethyl acetate using a rotary evaporator and purifying by column chromatography using a column packed with 25% aqueous silica gel to obtain 79.6 g of 3,4-epoxycyclohexane-1,2-dicarboxylic acid allyl.

Example 1

The interior of a 200 ml three-mouth flask provided with a reflux condenser, thermometer, stirring apparatus, dropping funnel and oil bath was adequately replaced with nitrogen gas. 21.9 g of the 4,5-epoxy-N-allylcyclohexane-1,2-dicarboximide obtained in Reference Example 1, 95.8 g of toluene and 50 μL of a 2-propanol solution of 0.1 mol/L chloroplatinic acid were charged therein. After sealing the end of the reflux condenser with nitrogen gas, the contents were heated to 100° C. while stirring and then maintained at that temperature. Next, 16.5 g of triethoxysilane were dropped in over the course of 1 hour. Following completion of dropping, the contents were further stirred for 10 hours. Following completion of the reaction, the solvent was removed using a rotary evaporator and the product was purified by column chromatography to obtain 35.9 g of the epoxy compound represented by the following formula (IV).

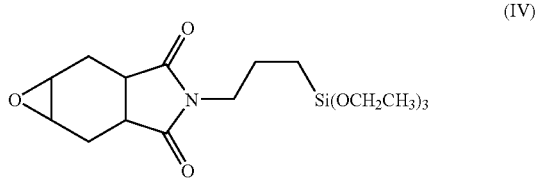

(IV)

Figure 2:
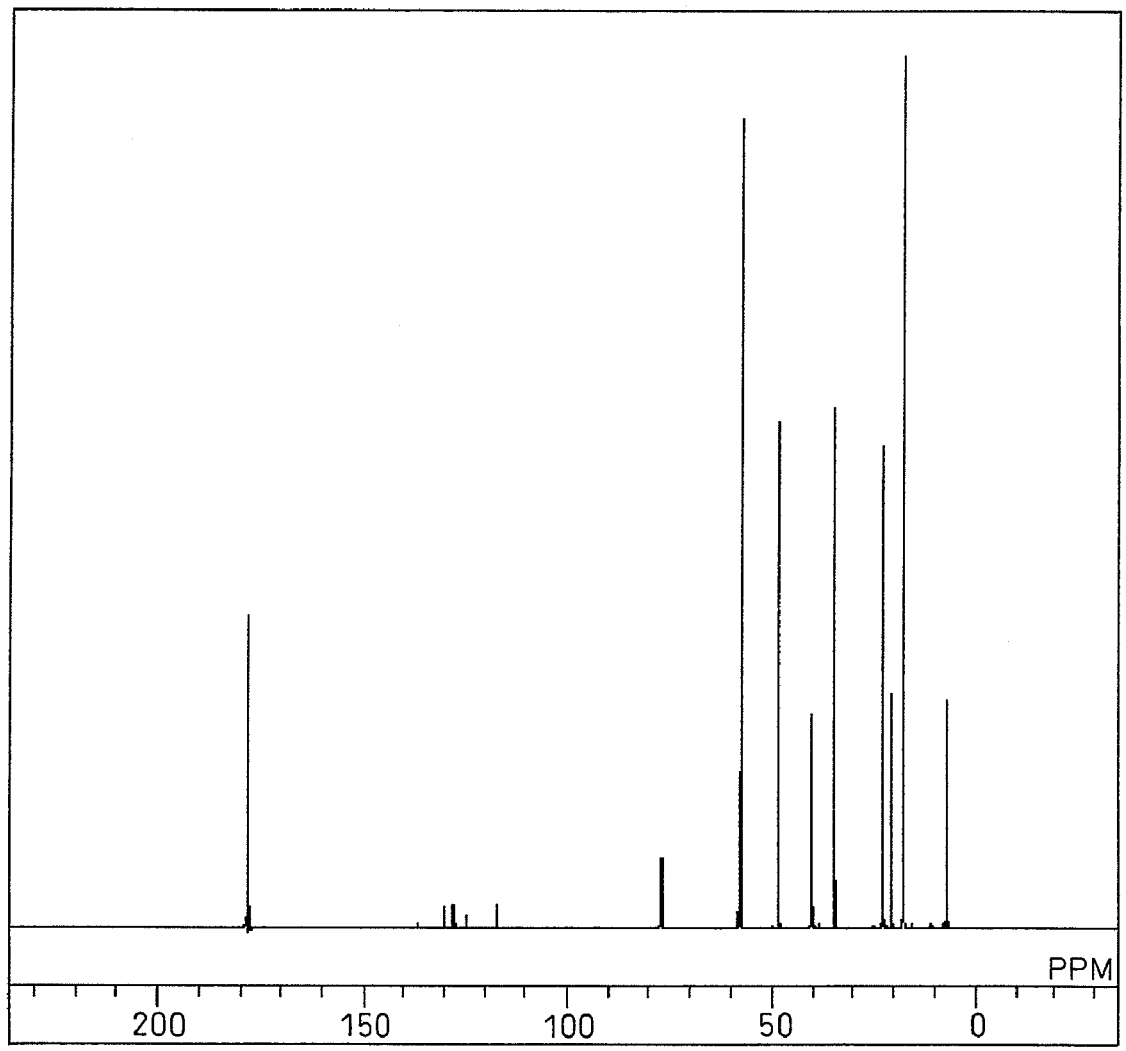
FIG. 2 is a chart showing the $^{13}$C-NMR spectrum of an epoxy compound represented by general formula (IV) obtained in Example 1.
Figure 3:
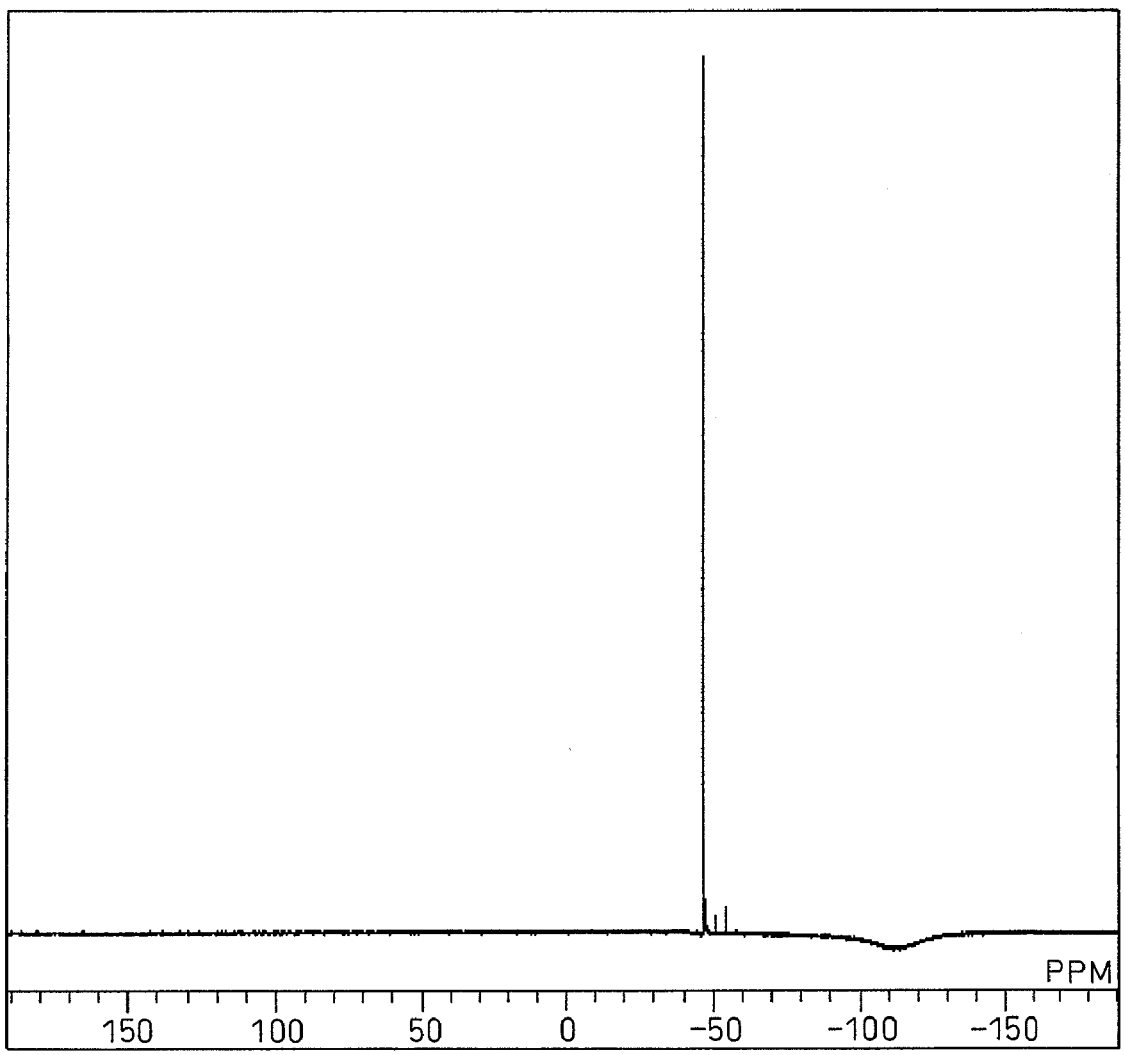
FIG. 3 is a chart showing the $^{29}$Si-NMR spectrum of an epoxy compound represented by general formula (IV) obtained in Example 1.

The structure of the epoxy compound represented by formula (IV) was able to be confirmed by measuring the $^1$H-NMR, $^{13}$C-NMR and $^{29}$Si-NMR spectra thereof in deuterated chloroform solvent using the AL-400 Nuclear Magnetic Resonance System manufactured by JEOL Ltd. The $^1$H-NMR, $^{13}$C-NMR and $^{29}$Si-NMR spectra of the epoxy compound represented by formula (IV) are shown in FIGS. 1, 2 and 3, respectively.

Example 2

The interior of a 200 ml three-mouth flask provided with a reflux condenser, thermometer, stirring apparatus, dropping funnel and oil bath was adequately replaced with nitrogen gas. 21.9 g of the 4,5-epoxy-N-allylcyclohexane-1,2-dicarboximide obtained in Reference Example 1, 95.8 g of toluene and 50 μL of a 2-propanol solution of 0.1 mol/L chloroplatinic acid were charged therein. After sealing the end of the reflux condenser with nitrogen gas, the contents were heated to 60° C. while stirring and then maintained at that temperature. Next, 10.8 g of methyldimethoxysilane were dropped in over the course of 1 hour. Following completion of dropping, the contents were further stirred for 20 hours. Following completion of the reaction, the solvent was removed using a rotary evaporator and the product was purified by column chromatography to obtain 27.4 g of the epoxy compound represented by the following formula (V).

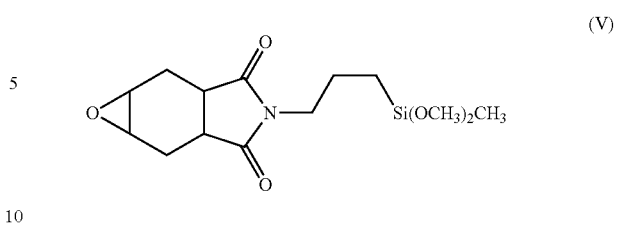

(V)

Figure 4:
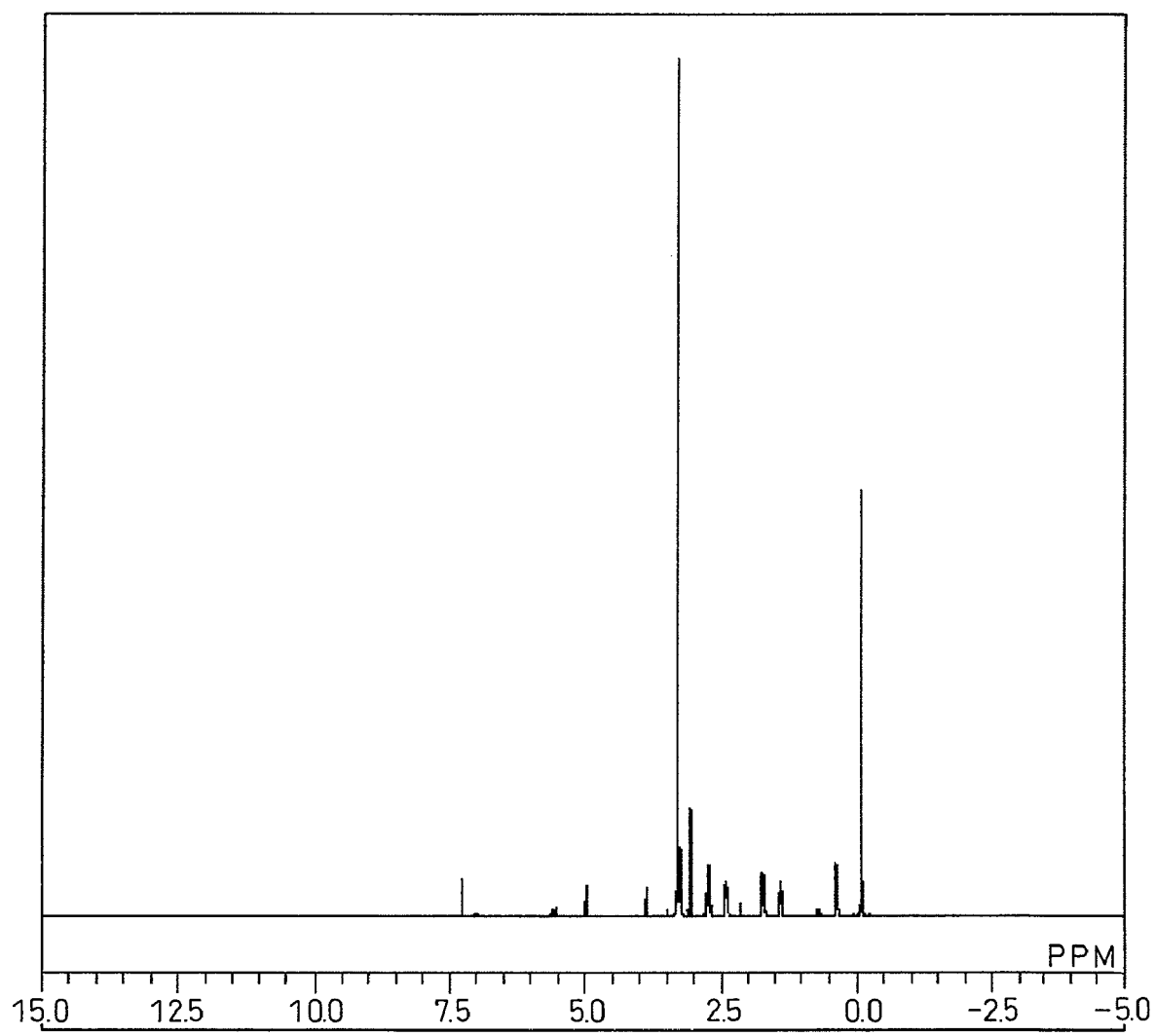
FIG. 4 is a chart showing the $^1$H-NMR spectrum of an epoxy compound represented by general formula (V) obtained in Example 2.
Figure 5:
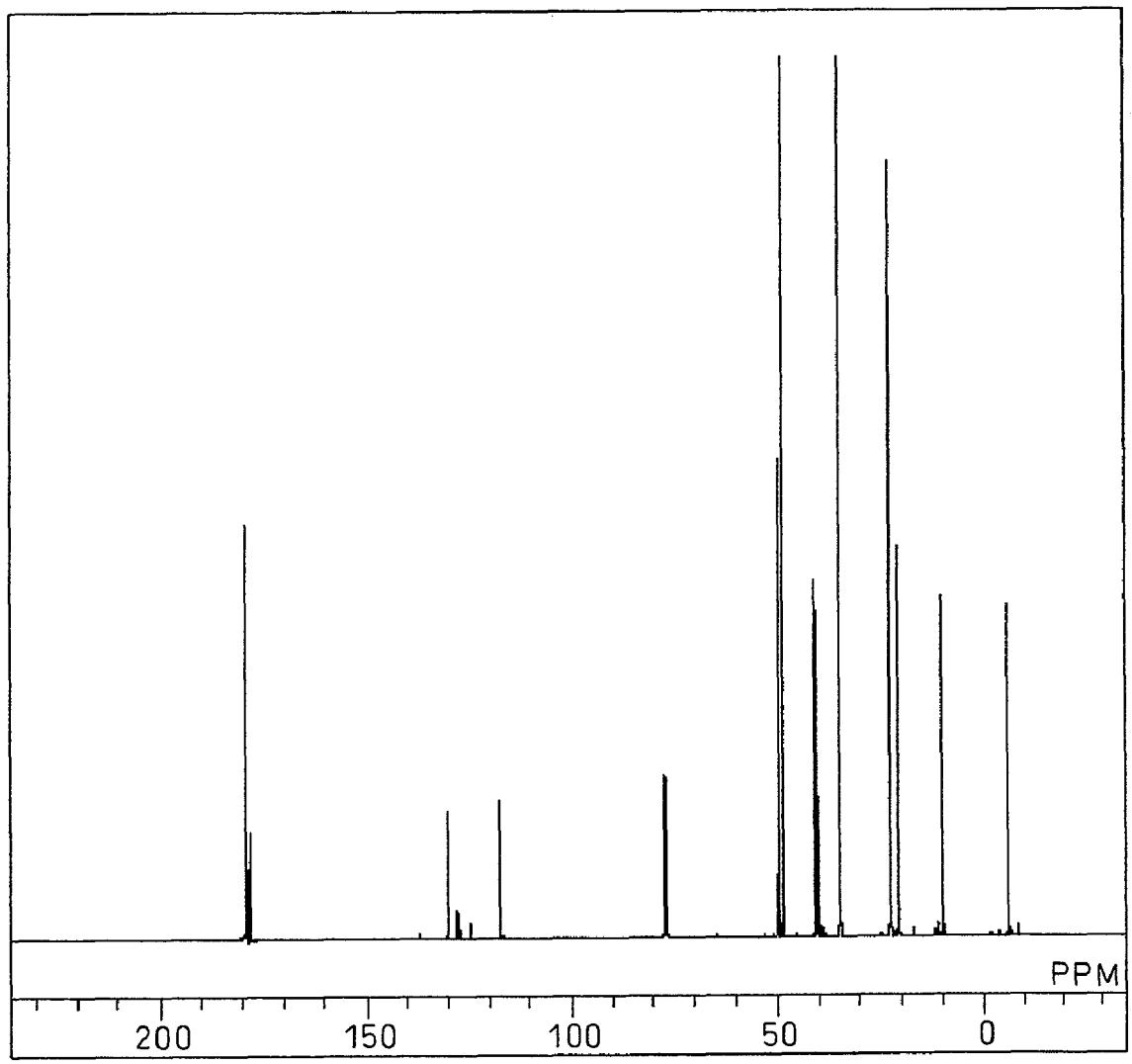
FIG. 5 is a chart showing the $^{13}$C-NMR spectrum of an epoxy compound represented by general formula (V) obtained in Example 2.
Figure 6:
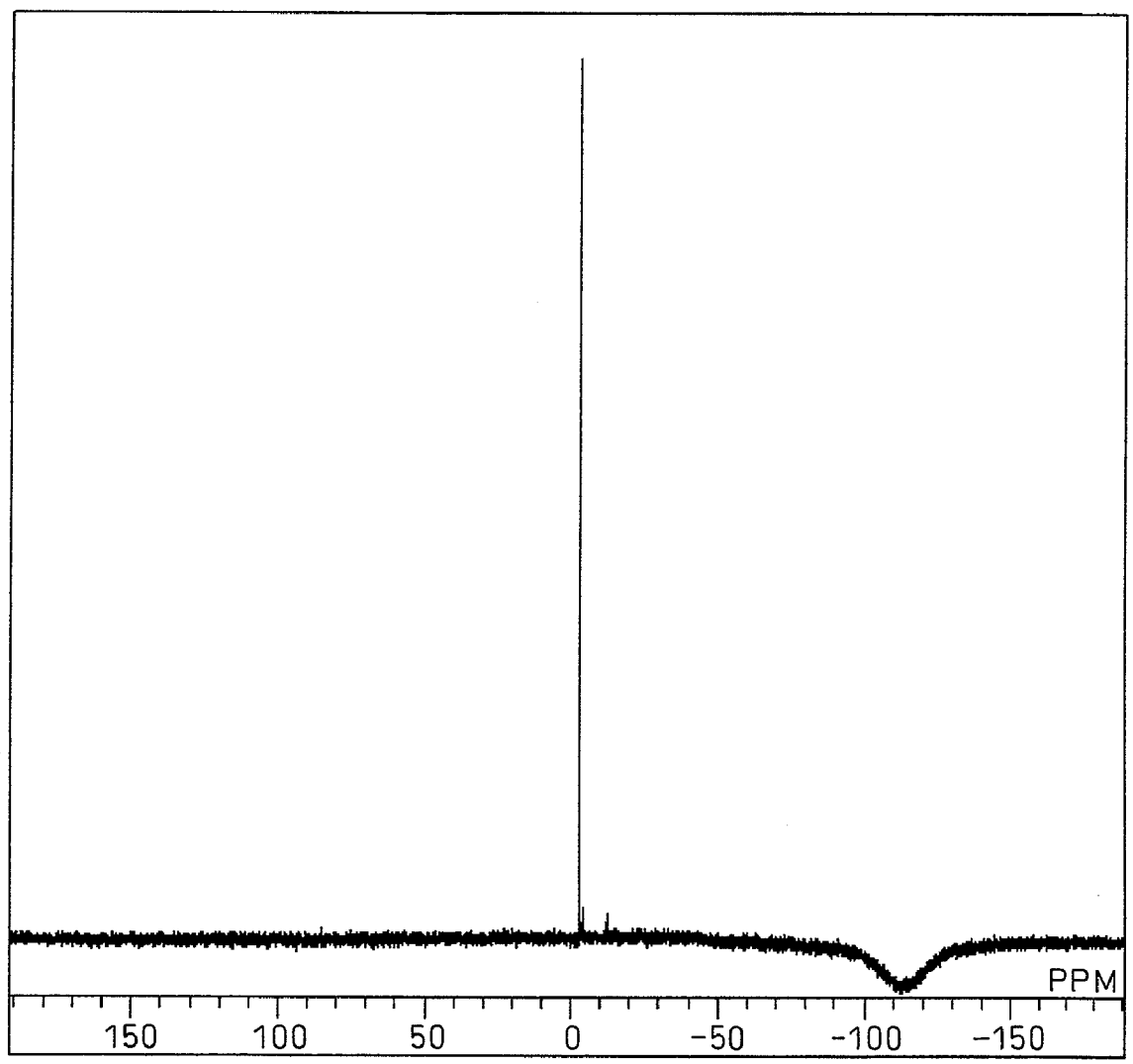
FIG. 6 is a chart showing the $^{29}$Si-NMR spectrum of an epoxy compound represented by general formula (V) obtained in Example 2.

The structure of the epoxy compound represented by formula (V) was able to be confirmed by measuring the $^1$H-NMR, $^{13}$-NMR and $^{29}$Si-NMR spectra thereof in deuterated chloroform solvent using the AL-400 Nuclear Magnetic Resonance System manufactured by JEOL Ltd. The $^1$H-NMR, $^{13}$C-NMR and $^{29}$Si-NMR spectra of the epoxy compound represented by formula (V) are shown in FIGS. 4, 5 and 6, respectively.

Example 3

The interior of a 100 ml three-mouth flask provided with a reflux condenser, thermometer, stirring apparatus, dropping funnel and oil bath was adequately replaced with nitrogen gas. 19.1 g of the 3,4-epoxycyclohexane-1-carboxylic acid allyl obtained in Reference Example 2 and 26 μL of a 2-propanol solution of 0.1 mol/L chloroplatinic acid were charged therein. After sealing the end of the reflux condenser with nitrogen gas, the contents were heated to 80° C. while stirring and then maintained at that temperature. Next, 16.5 g of triethoxysilane were dropped in over the course of 1 hour. Following completion of dropping, the contents were further stirred for 5 hours. Following completion of the reaction, the product was purified by column chromatography to obtain 34.1 g of the epoxy compound represented by the following formula (VI).

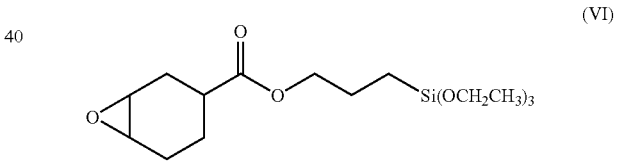

(VI)

Figure 7:
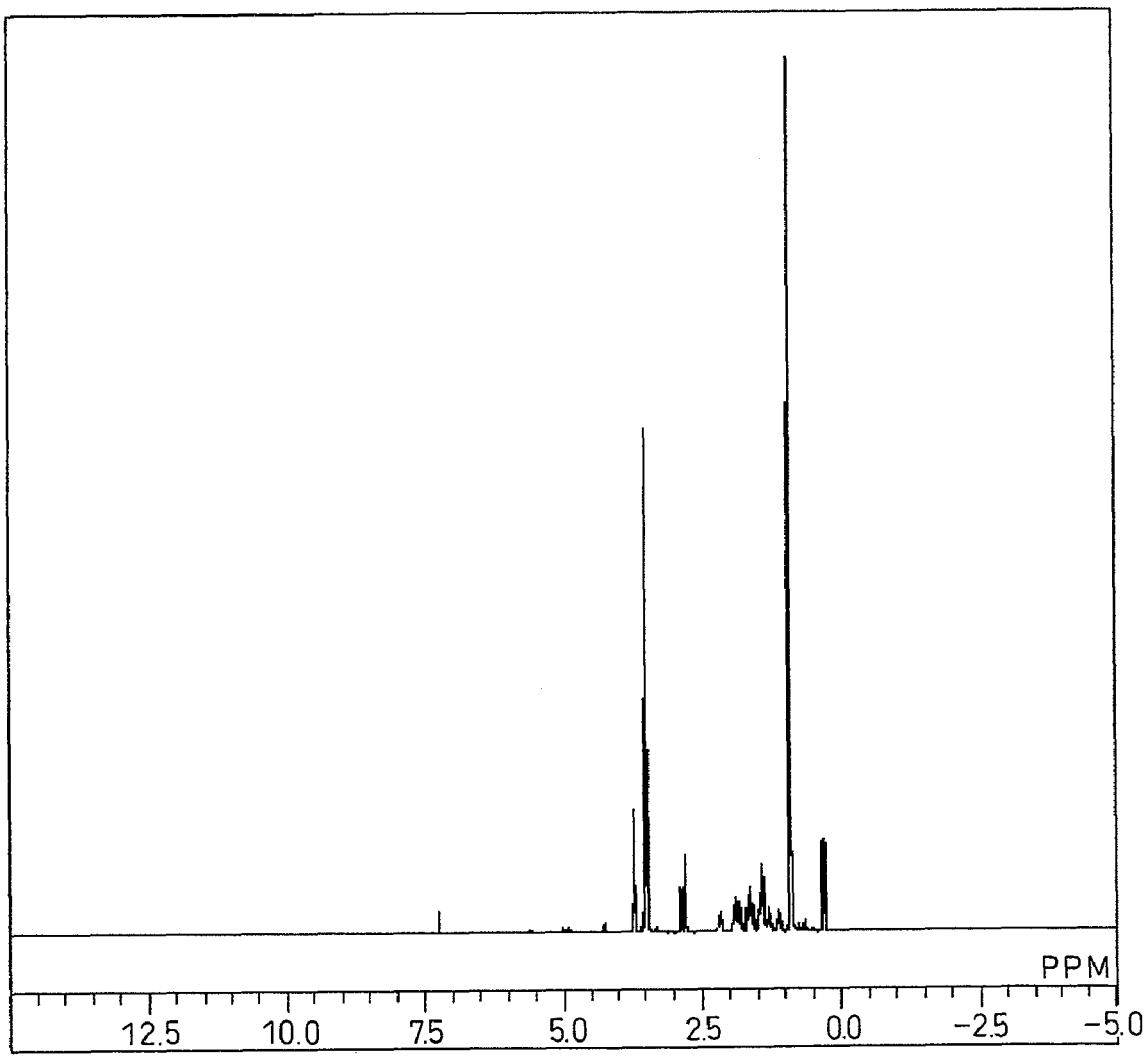
FIG. 7 is a chart showing the $^1$H-NMR spectrum of an epoxy compound represented by general formula (VI) obtained in Example 3.
Figure 8:
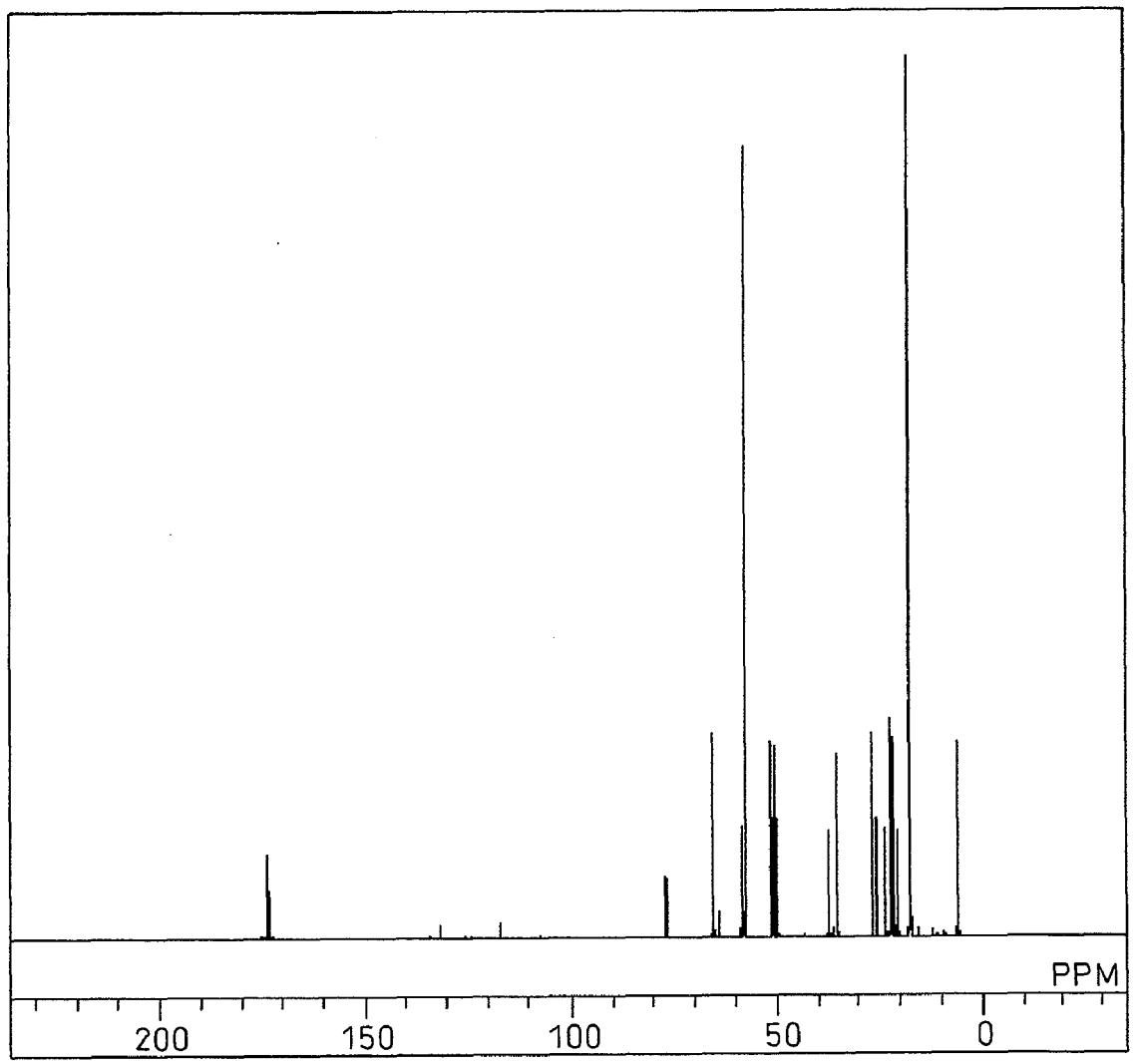
FIG. 8 is a chart showing the $^{13}$C-NMR spectrum of an epoxy compound represented by general formula (VI) obtained in Example 3.
Figure 9:
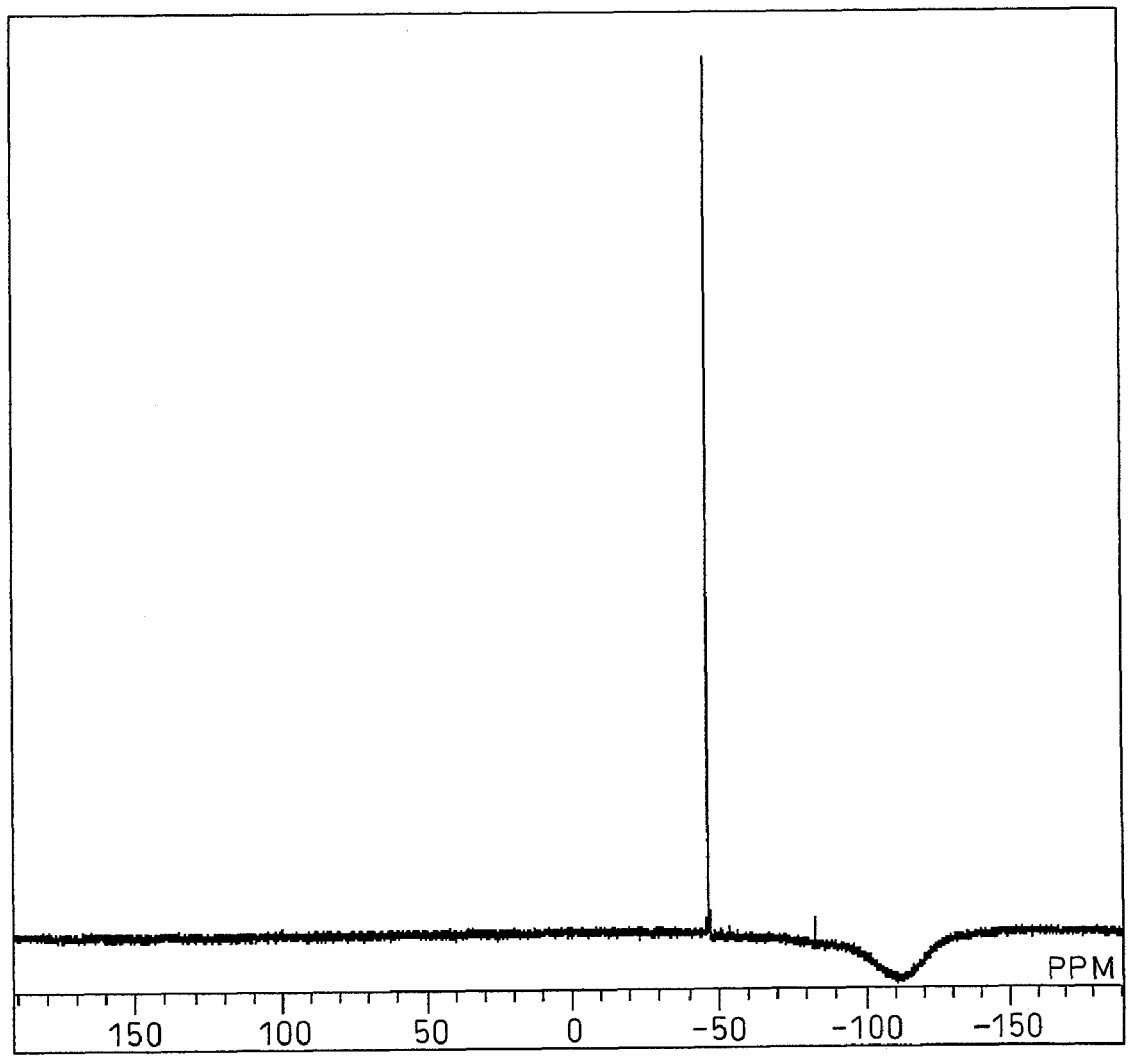
FIG. 9 is a chart showing the $^{29}$Si-NMR spectrum of an epoxy compound represented by general formula (VI) obtained in Example 3.

The structure of the epoxy compound represented by formula (VI) was able to be confirmed by measuring the $^1$H-NMR, $^{13}$C-NMR and $^{29}$Si-NMR spectra thereof in deuterated chloroform solvent using the AL-400 Nuclear Magnetic Resonance System manufactured by JEOL Ltd. The $^1$H-NMR, $^{13}$C-NMR and $^{29}$Si-NMR spectra of the epoxy compound represented by formula (VI) are shown in FIGS. 7, 8 and 9, respectively.

Example 4

The interior of a 100 ml three-mouth flask provided with a reflux condenser, thermometer, stirring apparatus, dropping funnel and oil bath was adequately replaced with nitrogen gas. 19.1 g of the 3,4-epoxycyclohexane-1-carboxylic acid allyl obtained in Reference Example 2 and 26 μL of a 2-propanol solution of 0.1 mol/L chloroplatinic acid were charged therein. After sealing the end of the reflux condenser with nitrogen gas, the contents were heated to 60° C. while stirring and then maintained at that temperature. Next, 10.8 g of methyldimethoxysilane were dropped in over the course of 1 hour. Following completion of dropping, the contents were further stirred for 14 hours. Following completion of the reaction, the product was purified by column chromatography to obtain 26.0 g of the epoxy compound represented by the following formula (VII).

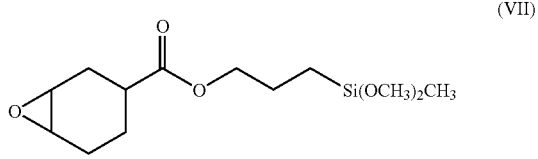

Figure 10:
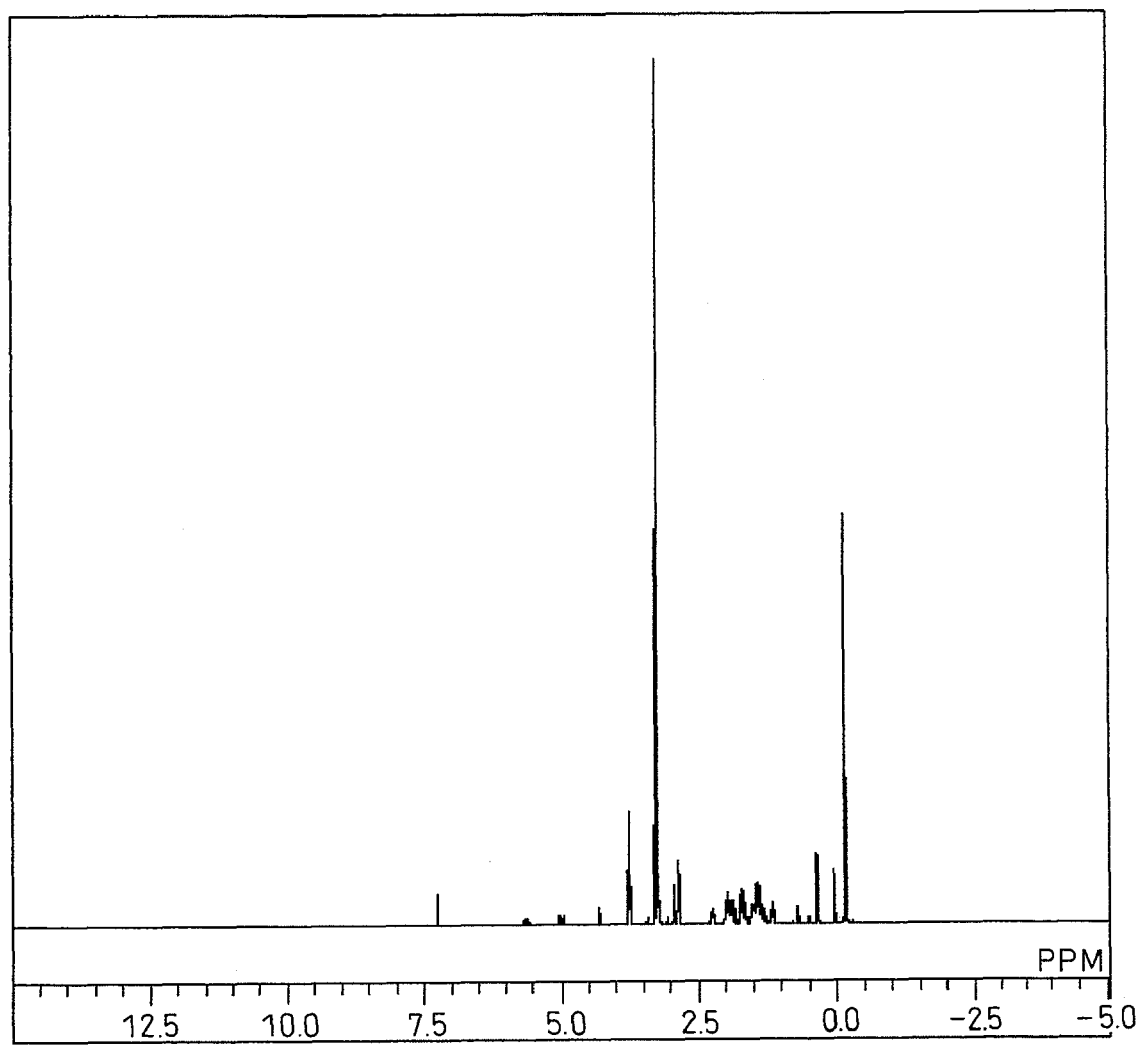
FIG. 10 is a chart showing the $^1$H-NMR spectrum of an epoxy compound represented by general formula (VII) obtained in Example 4.
Figure 11:
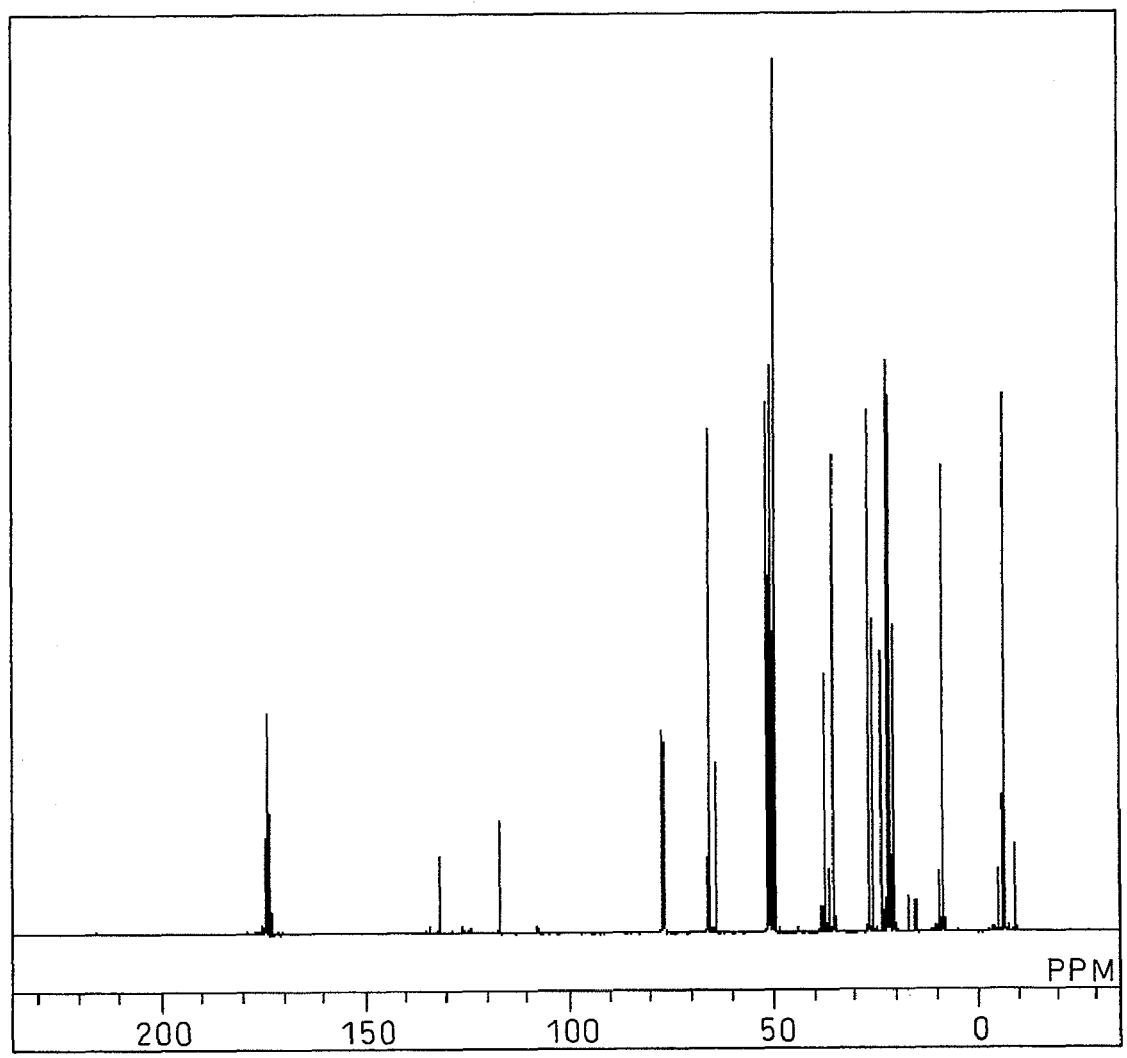
FIG. 11 is a chart showing the $^{13}$C-NMR spectrum of an epoxy compound represented by general formula (VII) obtained in Example 4.
Figure 12:
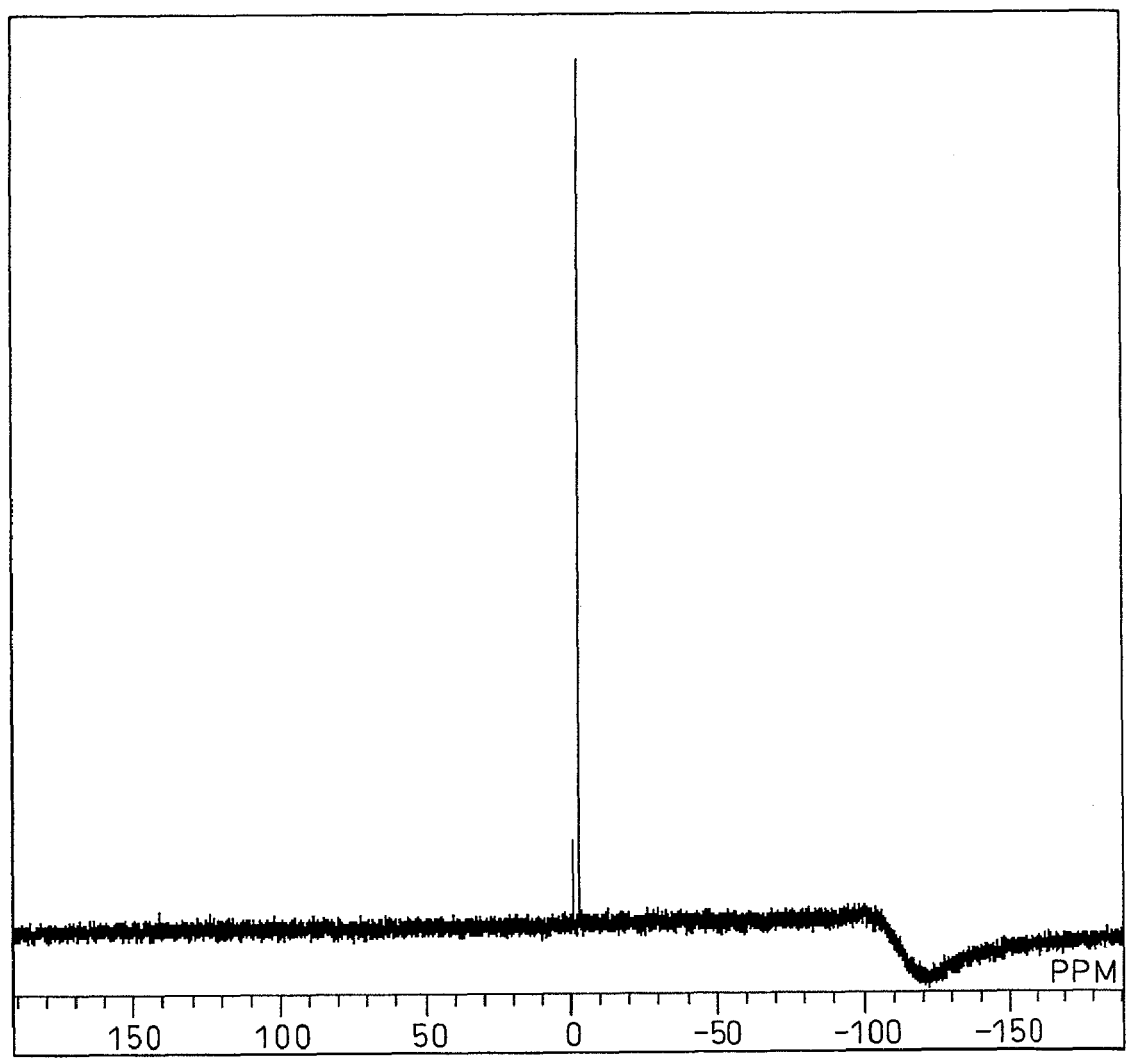
FIG. 12 is a chart showing the $^{29}$Si-NMR spectrum of an epoxy compound represented by general formula (VII) obtained in Example 4.

The structure of the epoxy compound represented by formula (VII) was able to be confirmed by measuring the $^{1}$H-NMR, $^{13}$C-NMR and $^{29}$Si-NMR spectra thereof in deuterated chloroform solvent using the AL-400 Nuclear Magnetic Resonance System manufactured by JEOL Ltd. The $^{1}$H-NMR, $^{13}$C-NMR and $^{29}$Si-NMR spectra of the epoxy compound represented by formula (VII) are shown in FIGS. 10, 11 and 12, respectively.

INDUSTRIAL APPLICABILITY

The novel epoxy compound of the present invention is useful in a wide range of fields such as sealing materials, formed materials, injection molding materials, laminated materials, composite materials, adhesives and powder coatings of electrical, electronic or optical components.

The invention claimed is:

1. An epoxy compound represented by the following general formula (I):

(wherein, Y is represented by any of the following formulas:

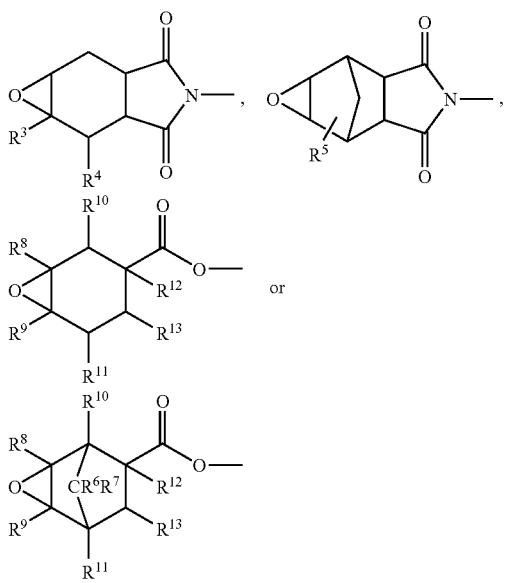

wherein, $R^1$ and $R^2$ represent alkyl groups having 1 to 5 carbon atoms, n represents an integer of 1 to 3, $R^3$ and $R^4$ represent hydrogen atoms, alkyl groups having 1 to 6 carbon atoms or trialkylsilyl groups having 1 to 4 carbon atoms, $R^5$ represents a hydrogen atom, an alkyl group having 1 to 6 carbon atoms or a trialkylsilyl group having 1 to 4 carbon atoms, $R^6$ to $R^{12}$ represent hydrogen atoms, alkyl groups having 1 to 6 carbon atoms or trialkylsilyl groups having 1 to 4 carbon atoms, and $R^{13}$ represents a hydrogen atom, an alkyl group having 1 to 6 carbon atoms, a trialkylsilyl group having 1 to 4 carbon atoms or an aryl group).

2. The epoxy compound of general formula (I) according to claim 1, wherein $R^1$ and $R^2$ are alkyl groups having 1 or 2 carbon atoms in the compound of general formula (I).

3. The epoxy compound of general formula (I) according to claim 1, wherein $R^3$ to $R^{12}$ are hydrogen atoms or methyl groups and $R^{13}$ is a hydrogen atom, methyl group or phenyl group in the compound of general formula (I).

4. The epoxy compound of general formula (I) according to claim 1, wherein $R^1$ and $R^2$ are alkyl groups having 1 or 2 carbon atoms, $R^3$ to $R^{12}$ are hydrogen atoms or methyl groups, and $R^{13}$ is a hydrogen atom, methyl group or phenyl group in the compound of general formula (I).

5. A production process of the epoxy compound of general formula (I) according to claim 1, comprising: reacting a silicon compound represented by the following general formula (II):

(wherein, $R^1$ and $R^2$ respectively represent an alkyl group having 1 to 5 carbon atoms, and n represents an integer of 1 to 3), with an epoxy compound having a double bond represented by the following general formula (III):

(wherein, Y is represented by any of the following formulas:

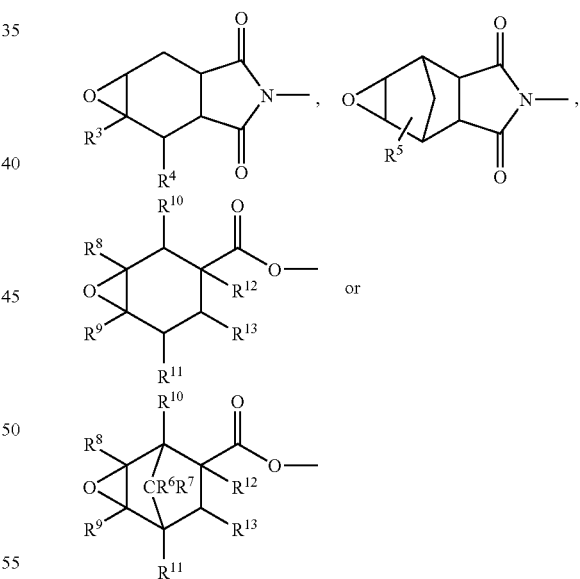

(wherein, $R^3$ and $R^4$ represent hydrogen atoms, alkyl groups having 1 to 6 carbon atoms or trialkylsilyl groups having 1 to 4 carbon atoms, $R^5$ represents a hydrogen atom, an alkyl group having 1 to 6 carbon atoms or a trialkylsilyl group having 1 to 4 carbon atoms, $R^6$ to $R^{12}$ represent hydrogen atoms, alkyl groups having 1 to 6 carbon atoms or trialkylsilyl groups having 1 to 4 carbon atoms, and $R^{13}$ represents a hydrogen atom, an alkyl group having 1 to 6 carbon atoms, a trialkylsilyl group having 1 to 4 carbon atoms or an aryl group) at 40 to 150° C.

6. The production process according to claim 5, wherein $R^1$ and $R^2$ are alkyl groups having 1 or 2 carbon atoms in the silicon compound of general formula (II).

7. The production process according to claim 5, wherein $R^3$ to $R^{12}$ are hydrogen atoms or methyl groups and $R^{13}$ is a hydrogen atom, methyl group or phenyl group in the epoxy compound having a double bond of formula (III).

8. The production process according to claim 5, wherein $R^1$ and $R^2$ are alkyl groups having 1 or 2 carbon atoms in the silicon compound of general formula (II), and $R^3$ to $R^{12}$ are hydrogen atoms or methyl groups and $R^{13}$ is a hydrogen atom, methyl group or phenyl group in the epoxy compound having a double bond of general formula (III).

* * * * *